(12) United States Patent
Brack et al.

(10) Patent No.: US 10,561,345 B2
(45) Date of Patent: Feb. 18, 2020

(54) DETERMINATION OF CENTER OF ROTATION OF A BONE

(71) Applicant: Brainlab AG, Munich (DE)

(72) Inventors: Christian Brack, Neusaess (DE); Mario Schubert, Poing (DE)

(73) Assignee: BRAINLAB AG, Munich (DE)

( * ) Notice: Subject to any disclaimer, the term of this patent is extended or adjusted under 35 U.S.C. 154(b) by 46 days.

(21) Appl. No.: 15/767,336

(22) PCT Filed: Dec. 11, 2015

(86) PCT No.: PCT/EP2015/079412
§ 371 (c)(1),
(2) Date: Apr. 10, 2018

(87) PCT Pub. No.: WO2017/097376
PCT Pub. Date: Jun. 15, 2017

(65) Prior Publication Data
US 2018/0296133 A1 Oct. 18, 2018

(51) Int. Cl.
*A61B 5/00* (2006.01)
*A61B 5/107* (2006.01)
(Continued)

(52) U.S. Cl.
CPC .......... *A61B 5/1121* (2013.01); *A61B 5/1127* (2013.01); *A61B 5/4504* (2013.01);
(Continued)

(58) Field of Classification Search
None
See application file for complete search history.

(56) References Cited

U.S. PATENT DOCUMENTS 6,692,447 B1 2/2004 Picard
7,535,411 B2 5/2009 Falco
(Continued)

FOREIGN PATENT DOCUMENTS

EP 1806109 B1 7/2007
WO WO2015022037 A1 2/2015

OTHER PUBLICATIONS

International Search Report and Written Opinion issued in International Application No. PCT/EP2015/079412 dated Aug. 12, 2016.
(Continued)

*Primary Examiner* — Idowu O Osifade
(74) *Attorney, Agent, or Firm* — Middleton Reutlinger

(57) ABSTRACT

A computer implemented method for determining a center of rotation of a bone, comprising the steps of: a) acquiring image data representing a plurality of images taken by a camera while the bone is being rotated about the center of rotation, wherein the images show a marker device attached to the bone; b) forming a plurality of image pairs from the image data, wherein each image pair comprises two different images; c) determining a first relative position of the marker device relative to the camera from a first image of an image pair; d) determining a second relative position of the marker device relative to the camera from a second image of the same image pair; e) calculating a transformation of the first relative position into the second relative position; f) repeating steps c) to e) for all image pairs to obtain a plurality of transformations; and calculating the location of the center of rotation of the bone relative to the marker device from the plurality of transformations.

15 Claims, 4 Drawing Sheets

(51) Int. Cl.
*A61B 5/11* (2006.01)
*G06T 7/00* (2017.01)
(52) U.S. Cl.
CPC .......... *A61B 5/1079* (2013.01); *A61B 5/4528* (2013.01); *A61B 5/6878* (2013.01); *G06T 7/0012* (2013.01)

(56) References Cited

U.S. PATENT DOCUMENTS

| | | |
|---|---|---|
| 2007/0239281 A1 | 10/2007 | Gotte et al. |
| 2009/0028296 A1 | 1/2009 | Graumann et al. |
| 2011/0054851 A1 | 3/2011 | Heller et al. |
| 2011/0169861 A1 | 7/2011 | Suzuki et al. |
| 2011/0282473 A1* | 11/2011 | Pavlovskaia ............. G06K 9/48 700/98 |
| 2012/0029389 A1 | 2/2012 | Amiot et al. |
| 2013/0201291 A1 | 8/2013 | Liu et al. |
| 2015/0223753 A1 | 8/2015 | Perkins et al. |

OTHER PUBLICATIONS

McGinnis, et al. "Intertial Sensor Based Method for Identifying Spherical Joint Center of Rotation" Journal of Biomechanics, Issue 46. 2013.
Siston et al. "Evaluation of a New Algorithm to Determine the Hip Joint Center" Journal of Biomechanics, Issue 39. 2006.

* cited by examiner

DETERMINATION OF CENTER OF ROTATION OF A BONE

TECHNICAL FIELD

The present invention relates to a computer implemented method for determining a center of rotation of a bone and to a corresponding computer program and system.

SUMMARY

Two adjacent bones in a body, for example a human body, are typically connected via a joint. This joint typically enables a relative rotation between the bones about a center of rotation. A typical type of joint enables a rotation in one rotational dimension, such that the center of rotation is an axis. Another type of joint is a ball-and-socket joint, which enables a rotation in three rotational dimensions. A ball-and-socket type of joint can for example be found between a femur and a pelvis or between a humerus and a scapula.

There are many medical applications which require the center of rotation of a joint to be known. In those applications, a marker device is typically attached to at least one of the bones which form the joint. The location of the center of rotation is then for example defined relative to the marker device, and is therefore referred to as the center of rotation of the bone. If the bone is a femur, the center of rotation of the femur typically is the center of the femoral head. If the bone is a humerus, then the center of rotation of the humerus typically is the center of the humeral head.

One typical application in which the center of rotation of a bone has to be known is a partial or full joint replacement in which a part of the bone which forms the joint or a part of the joint is replaced by an implant. The goal is for example to maintain the mechanical axis of the bone after the replacement. In general, the application can be the preparation of a surgical intervention.

In this document, a femur is used as a bone whose center of rotation is to be determined. However, this is only exemplary for an easier description of the invention.

The present invention aims at providing an approach for determining a center of rotation of a bone by analyzing images of a marker device which is (for example rigidly) attached to the bone. A marker device being rigidly attached to a bone means that a relative movement between the marker device and the bone is prevented as far as possible in the context of a medical application. It does for example mean that the marker device is screwed or bolted to the bone. However, the process of attaching the marker device to the bone is only preparatory for the present invention and not a part of the present invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a computer implemented method for determining a center of rotation of a bone. The method comprises a first step of acquiring image data representing a plurality of images taken by a camera while the bone is being rotated about the center of rotation, wherein the images show a marker device attached to the bone. The images can be 2D or 3D images, wherein the marker device is designed such that its position in up to three translational dimensions and/or up to three rotational dimensions can be determined from an image. The plurality of images are taken at different points in time, for example at equidistant points in time.

Rotating the bone about the center of rotation can also be referred to as pivoting the bone. For the present invention, it is assumed that the center of rotation remains stationary while the bone is pivoted. This does for example mean that another bone to which the bone is connected via the joint is considered to remain stationary.

The method comprises a second step of forming a plurality of image pairs from the image data, wherein each image pair comprises two different images. A particular image can be assigned to two or more image pairs. In one example, there are no two identical image pairs, that is pairs comprising the same two images. An image of one image pair can lie between the two images of another image pair. It is possible, but not mandatory, that each image of the image data is assigned to at least one image pair.

The method comprises a third step of determining a first relative position of the marker device relative to the camera from a first image of an image pair. It further comprises a fourth step of determining a second relative position of the marker device relative to the camera from a second image of the same image pair. This means that the first relative position is associated with the first image of the image pair and the second relative position is associated with the second image of the image pair.

The method further comprises a fifth step of calculating a transformation of the first relative position into the second relative position. This transformation describes the movement of the marker device relative to the camera between the point in time at which the first image of the image pair was captured and the point in time at which the second image of the image pair was captured.

The method further comprises a sixth step of repeating the third step, the fourth step and the fifth step for all image pairs to obtain a plurality of transformations. In this step, the expression "all image pairs" means all image pairs out of the plurality of image pairs formed in the second step.

The method further comprises a seventh step of calculating the location of the center of rotation of the bone relative to the marker device from the plurality of transformations.

According to the present invention, the center of rotation is not determined from a plurality of positions of the marker device determined from the plurality of images. The invention rather calculates a plurality of transformations of the marker device from a plurality of image pairs formed from the image data and then calculates the center of rotation from the plurality of transformations.

If the camera is stationary during the time period in which the plurality of images represented by the image data were taken, then each of the plurality of transformations describes a rotation of the marker device about the center of rotation of the bone. It is therefore possible to calculate the center of rotation in a known manner.

However, if the camera is not stationary, each transformation of the plurality of transformations might not only represent a rotation of the marker device about the center of rotation, but also depends on the displacement of the camera. In one embodiment, the method therefore further comprises the step of determining, for each image pair, a displacement of the camera between the points in time at which the images of the respective image pair were captured. The term "displacement" means a movement of the camera in up to three rotational dimensions and/or up to three translational dimensions.

In one embodiment, calculating the center of rotation in the seventh step involves weighting the transformations depending on the displacements of the camera associated with the corresponding image pairs. In a simple example, a weight of zero is applied to a transformation associated with an image pair comprising images between which the camera has moved. This means that the camera has moved between the points in time at which the first and second images of this image pair have been captured. Another example relates to applying a weight which is inversely proportional to a metric of the displacement of the camera. The metric is for example the larger the larger the translational component and/or the rotational component of the displacement is.

In another embodiment, the method further comprises the step of amending the first relative position or the second relative position associated with an image pair to compensate the displacement of the camera if the displacement associated with the corresponding image pair is above a predetermined threshold. This threshold can for example be zero, which means that any displacement of the camera is compensated. Compensating the displacement of the camera means that the displacement of the camera is neutralized by adapting the first relative position or the second relative position appropriately. In one example, amending a relative position, that is the first relative position or the second relative position, involves subtracting the displacement of the camera from the relative position or adding the displacement of the camera to the relative position.

When the first or second relative position is amended as explained above, the transformation in the fifth step is based on the amended relative position. This means that the step of amending the first relative position or the second relative position is preferably performed between the fourth step and the fifth step of the method.

There are many possible approaches for determining the displacement of the camera between the points in time at which the first image and the second image of an image pair have been captured.

In one embodiment, the displacement of the camera is calculated from sensor data acquired from an inertial sensor attached to the camera. In one example, acceleration data comprised in this sensor data is integrated between the points in time at which the first and second images of an image pair have been captured for obtaining the translation of the camera. This time span is typically much smaller than the time span during which the complete plurality of images has been captured, for example if an image pair comprises temporally consecutive images from the image data. The integration of the sensor data thus happens during a short time span, and does therefore reliably represent the displacement of the camera, which might not be the case for a long time span.

In one embodiment, the displacement of the camera is calculated from differences of positions within the first and second images of an image pair which show the same points in space, in particular the same fixed points in space. A fixed point in space means a point with a fixed position in space, which means a point in space which does not change its position between the points in time at which the first and second images were captured. If the camera is moved, the position of a point in space typically differs between the first and second images. If the positions of a plurality of points in space within the first and second images are determined, the displacement of the camera can be calculated from the differences of those positions. In this context, the term "difference" means the distance about and/or the direction in which the position has changed. The position is for example the position of a pixel which shows the point in space in an image.

In one embodiment, a point in space is not a point on a marker device.

Approaches for calculating the movement of a camera from positions in different images at which the same points in space are imaged are known to the skilled person. One possible implementation is briefly summarized below.

This exemplary approach is based on epipolar geometry of perspective projections assuming that the optical properties of the camera are known.

If a point in space is imaged at a particular position within an image, it is known that this point lies on a straight line in space, wherein the location and orientation of this straight line relative to the camera is known due to the optical properties of the camera. If the camera is displaced and a second image is taken, the point in space is imaged on a second line which is the projection of the straight line into the second image. In addition, this second line intersects with a third line which connects the positions of a particular point, such as the focal center, of the camera at the points in time at which the two images were taken. If a plurality of points in space is analyzed, the displacement of the camera can be calculated.

One exemplary implementation is based on the essential or fundamental matrix. The essential matrix E is defined as $$x'^T*E*x=0,$$

where x' and x are the projection points of a particular point in space in the two images in projective coordinates (x,y,1) ^T. The essential matrix is defined as $$E=tx*R_c,$$

where tx contains the translation vector in a skew form and $R_c$ is the rotation matrix between the camera positions. With this formula and enough points, tx and $R_c$ can be found. There are different algorithms to solve the equations, like polynominal, least squares or ransac (random sample consensus) minimizers.

In one embodiment, a pair of images comprises two consecutive images. This results in no or only a small displacement of the camera for the pair of images.

In another embodiment, the pair of images comprises two images which were taken at two points in time which differ by at least a predetermined threshold. This means that a certain amount of time has passed between capturing the two images of an image pair. It can then be assumed that the bone, and therefore the marker device, has moved by at least a certain amount.

In yet another embodiment, a pair of images comprises two images which fulfill a marker device movement criterion. This criterion defines that the marker device has moved by at least a certain amount relative to the camera between the points in time at which the two images were captured, for example by at least a predetermined rotation angle, such as 1°, 2°, 5° or 10°.

In still another embodiment, a movement detector is attached to the bone or to the marker device. The movement detector detects its movement in space, and thus the movement of the marker device and the bone. The movement detector is configured to transmit movement detection signals. It for example transmits a movement detection signal if the movement of the movement detector exceeds a predetermined threshold since the last transmission of a movement detection signal. Reception of a movement detection signal can trigger to capture an image for the image data. In addition or as an alternative, the image in the image data which was captured exactly at, or if there is no such image, next after transmission of a movement detection signal is marked accordingly. A pair of images for example comprises two images which are marked accordingly and have no other marked image in between, one marked image and one non-marked image with at least one marked image in between or two non-marked images with at least two marked images in between. The expression "in between" relates to a temporal order of the images.

In one embodiment, the transformation is represented by a 4×4 matrix. A plurality of such matrixes can easily be utilized in the seventh step of the method.

In one embodiment, the method further comprises the steps of forming additional image pairs, repeating the third, fourth and fifth steps for the additional image pairs, adding the transformations associated with the additional image pairs to the plurality of transformations, thus obtaining a new plurality of transformations, and repeating the seventh step for the new plurality of transformations. This embodiment is particularly advantageous if the accuracy of the location of the center of rotation is below a predetermined threshold.

The additional image pairs preferably do not comprise two identical image pairs and/or an image pair already comprised in the initial plurality of image pairs.

There is a plurality of approaches for determining the accuracy of the location of the center of rotation known to the skilled person.

In one implementation, a location of a center of rotation is determined from each transformation, resulting in a plurality of individual locations of the center of rotation. The differences between each of the individual locations of the center of rotation and the location of the center of rotation calculated from all transformations is statistically analyzed, which can comprise calculating the mean and/or the standard deviations of the differences. The accuracy of the location of the center of rotation is then determined from the result of the statistical analysis.

In another implementation, the (initial) image pairs are divided into subsets of image pairs and the center of rotation is determined for each of the subsets of transformations. The differences between the centers of rotation corresponding to the different subsets are representative of the accuracy of the location of the center of rotation.

In one embodiment, the relative position of the marker device relative to the camera is the position of a co-ordinate system associated with the marker device in a co-ordinate system associated with the camera. The co-ordinate system associated with the camera is a co-ordinate system which has a known location and orientation relative to the camera. The co-ordinate system associated with the marker device has a known location and orientation relative to the marker device. Since the marker device is attached to the bone, the co-ordinate system associated with the marker device has a fixed relative position relative to a co-ordinate system associated with the bone. The co-ordinate systems are for example Cartesian co-ordinate systems.

The position of the co-ordinate system associated with the marker device relative to the marker device is preferably known to the method.

In one embodiment, calculating a transformation of a first relative position into a second relative position in the fifth step of the method takes into account that the transformation is a rotation about a fixed point or axis in space. This is a constraint which limits the transformation. If the transformation is a rotation about a fixed point in space, then the marker device moves on a sphere while the bone is pivoted. If the transformation is a rotation about a fixed axis in space, then the marker device moves on a circular ark while the bone is pivoted.

The present invention also relates to a program which, when running on a computer, causes the computer to perform the method steps of the method described above and/or a program storage medium on which the program is stored, in particular in a non-transitory form.

The present invention further relates to a system comprising a computer on which the aforementioned program is stored and/or run.

DEFINITIONS

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

This invention will be part of a new development focusing on intelligent orthopedic instruments designed for a streamlined workflow. It will be used for an instrument supporting alignment of femur or other implants.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
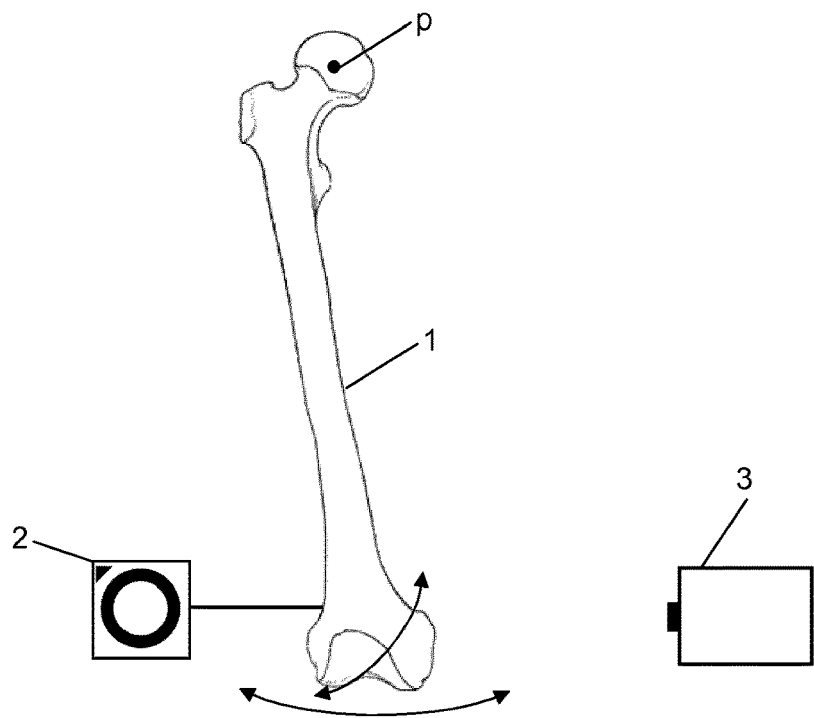
FIG. 1 a femur with a marker device attached.

FIG. 1 shows a femur 1 as an example of a bone for which the center of rotation is to be determined. Rigidly attached to the femur 1 is a marker device 2. The marker device 2 in this example comprises a carrier having a flat area on which an optical pattern is provided. The area bearing the optical pattern can also be a non-flat area. A camera 3 is provided to capture a plurality of images over time, the images showing the marker device 2.

The femur 1 forms a hip joint together with a pelvic bone (not shown). The hip joint is a ball-and-socket type of joint. The hip joint allows a rotation of the femur 1 about its center of rotation, which is shown as the point p in FIG. 1. In the case of a femur, the center of rotation typically is the center of the femoral head.

For many medical applications, for example in preparation of a surgical procedure, it might be necessary to know the location of the center of rotation, that is the point p, for example relative to the bone, in the present case the femur 1, or relative to the marker device 2 attached to the bone. Determining the center of rotation relative to the marker device 2 can also be referred to as a registration of the bone, or at least a partial registration of the bone.

The rotation of the femur 1 about the point p is indicated by the arrows in FIG. 1. It shall be noted that this rotation can basically occur in three rotational dimensions which are for example orthogonal to each other. Rotating the bone is also referred to as pivoting the bone.

Figure 2:
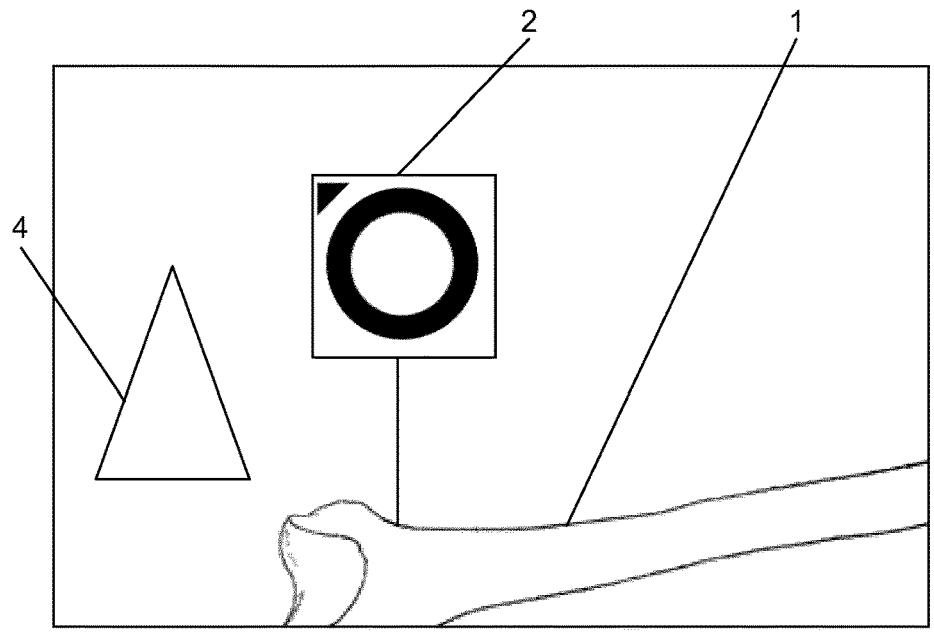
FIG. 2 an exemplary camera image.

FIG. 2 shows an exemplary output image of the camera 3. This exemplary output image depicts a part of the femur 1 and at least the optical pattern on the surface of the marker device 2. The camera image further depicts other points in space, such as points belonging to an object 4.

The optical pattern on the surface of the marker device 2 is known. In addition, the optical properties of the camera 3 are known. The relative position of the marker 2 relative to the camera 3 can then be calculated in up to three translational dimensions and/or up to three rotational dimensions from the camera image depicting the optical pattern. This technique is known to the skilled person.

In order to determine the relative position between the camera 3 and the marker device 2, references must be assigned to the camera 3 and the marker device 2. In this exemplary embodiment, a camera co-ordinate system is assigned to the camera 3, having a known spatial relation to the camera 3. In addition, a marker device co-ordinate system is assigned to the marker device 2, having a known spatial relation to the marker device 2, and therefore to the optical pattern on the marker device 2. The relative position between the camera 3 and the marker device 2 is then given as the position of the co-ordinate system assigned to the marker device 2 in the co-ordinate system assigned to the camera 3.

Figure 3:
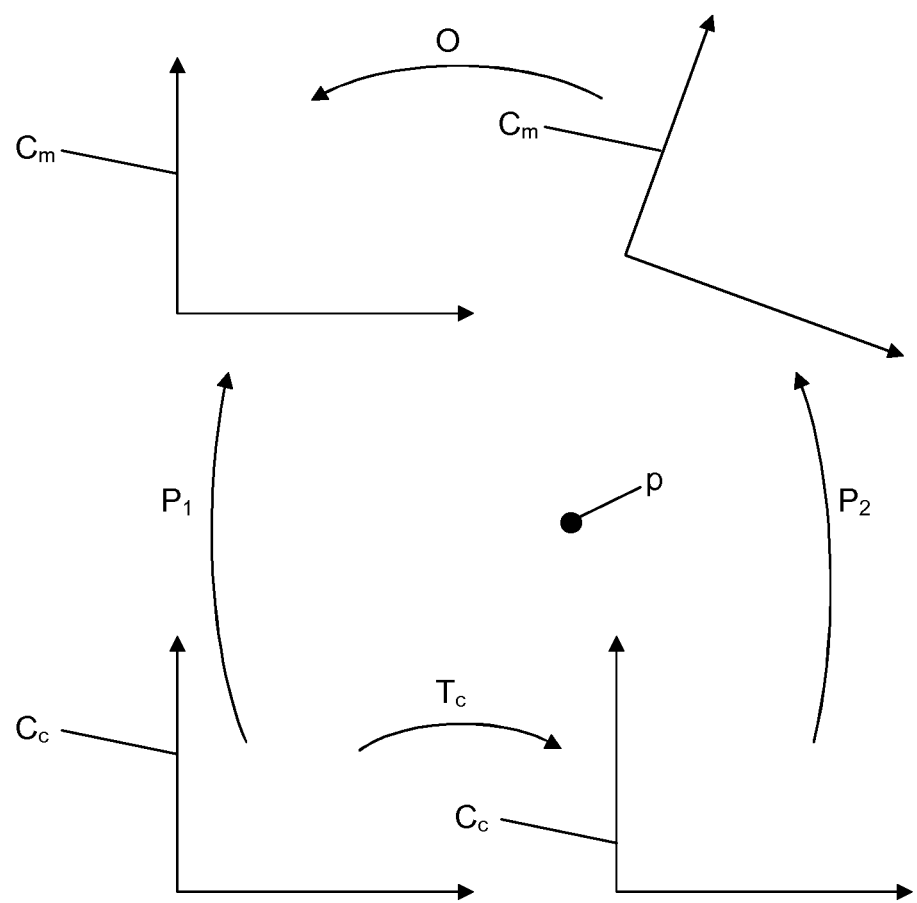
FIG. 3 exemplary camera and marker device positions.

FIG. 3 schematically shows the relation between the two co-ordinate systems for two different images taken at two different points in time between which the femur 1 has been pivoted about its center of rotation p. In FIG. 3, the situation is shown in two dimensions only to simplify the illustration, but it is actually three-dimensional.

FIG. 3 shows the position of the co-ordinate system $C_m$ associated with the marker device 2 in the co-ordinate system $C_c$ associated with the camera 3. The left part of FIG. 3 shows the relative position $P_1$ at a first point in time and the right part of FIG. 3 shows the relative position $P_2$ at a second point in time. In the illustration of FIG. 3, the camera 3 has moved between those two points in time, resulting in a displacement or transformation $T_c$. If the camera has not moved, then $T_c=0$.

As outlined above, the relative positions $P_1$ and $P_2$ can be determined from two camera images. The displacement $T_c$ of the camera 3 can also be determined. This means that the movement of the marker device 2 in space between the two points in time, which is indicated as O in FIG. 3, can be calculated as $O=P_1*T_c^{-1}*P_2^{-1}$. This movement or transformation O represents the movement of the marker device 2 in space, which is known to be a rotation about the point p.

Figure 4:
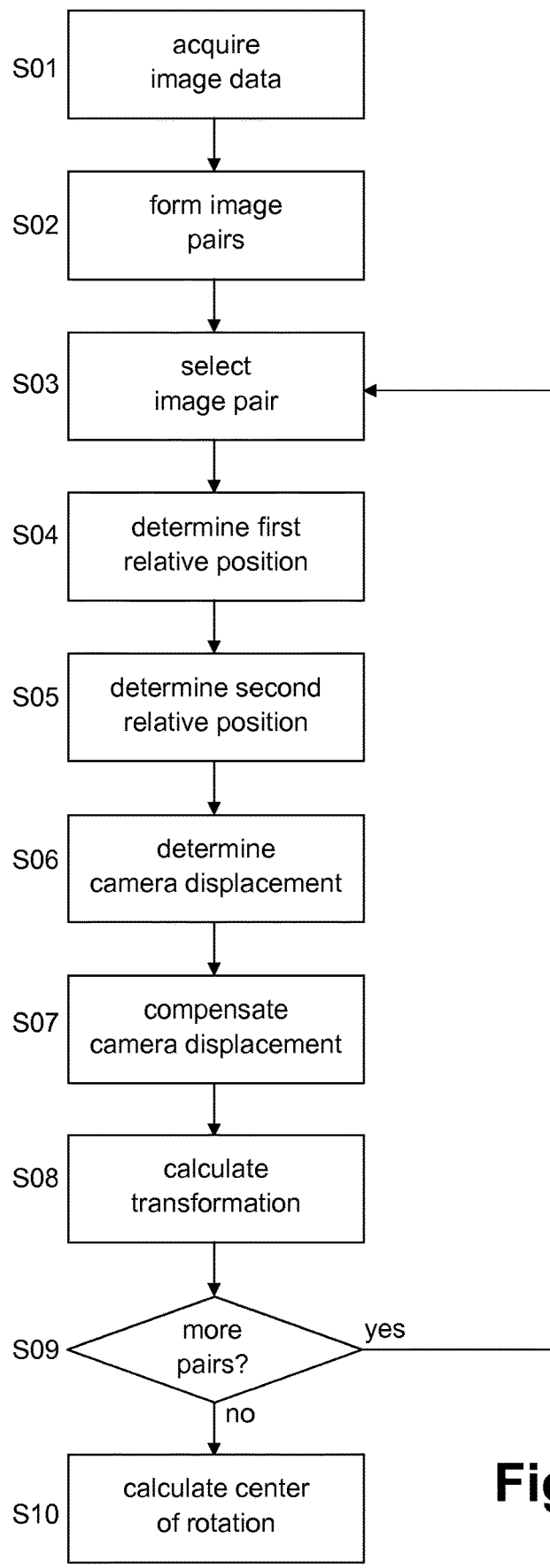
FIG. 4 a flow diagram of a method for determining a center of rotation of a bone and FIG. 5 a system on which the method is implemented.

FIG. 4 shows a flow diagram of a method for determining the center of rotation p of the femur 1 as an example of a general center of rotation of a bone.

Step S01 involves acquiring image data representing a plurality of images taken by the camera 3 while the femur 1 is being rotated about the center of rotation p. Each of the plurality of images is taken at a different point in time, and the image data preferably, but not necessarily, represents the plurality of images in their temporal order. The images show the marker device 2 attached to the femur 1. In the present embodiment, the camera 3 is a camera which captures two-dimensional images.

Step S02 involves forming a plurality of image pairs from the image data, wherein each image pair comprises two different images. This means that the two images of an image pair are taken at different points in time, which from now on are referred to as t1 and t2. It is possible, but not mandatory, that each image out of the plurality of images is assigned to an image pair. An image of the plurality of images can be assigned to more than one image pair.

Step S03 involves selecting an image pair from the plurality of image pairs. In particular, an image pair is selected which has not yet previously been selected out of the plurality of image pairs.

Step S04 involves determining a first relative position of the marker device 2 relative to the camera 3 from the first image of the image pair selected in step S03. Step S05 involves determining a second relative position of the marker device 2 relative to the camera 3 from the second image of the image pair selected in step S03. The relative positions are determined by analyzing the images in order to find the optical pattern of the marker device 2 and its shape in the images as explained with reference to FIG. 2.

Step S06 involves determining a displacement of the camera between t1 and t2. Step S07 then involves compensating the displacement $T_c$ of the camera 3 determined in step S06. In FIG. 3, the displacement of the camera is shown as $T_c$. Step S07 in particular involves adding the displacement $T_c$ of the camera 3 to the first relative position $P_1$ determined in step S04 or subtracting the displacement $T_c$ of the camera 3 from the second relative position $P_2$ determined in step S05.

Step S08 involves calculating a transformation, which is indicated as O in FIG. 3, of the first relative position $P_1$ into the second relative position $P_2$. This transformation is associated with the image pair selected in step S03. Details of step S08 were already described with reference to FIG. 3.

Step S09 involves determining whether or not there are more image pairs, which means image pairs for which no transformation has been calculated yet. If this is the case, the method returns to step S03, where a new image pair is selected and steps S04 to S08 are performed for the new image pair in order to calculate a transformation associated with the new image pair. This means that the method iterates through the image pairs. If there are no more image pairs, the method continues with step S10, which involves calculating the center of rotation p of the femur 1. If transformations for N image pairs, wherein N is a positive integer, have been calculated, those transformations are referred to as $O_1$ to $O_N$.

In one implementation, the transformation O is given as a 4×4 matrix $$O = \begin{pmatrix} R & T \\ 0 & 1 \end{pmatrix},$$

wherein R is a 3×3 matrix describing a rotation and T is a 1×3 matrix describing a translation. The point p, given in co-ordinates defined relative to the co-ordinate system $C_m$ associated with the marker device 2, is written as the vector $$p' = \begin{pmatrix} x \\ y \\ z \\ 1 \end{pmatrix},$$

wherein x, y and z are the co-ordinates of the point p in the co-ordinate system $C_m$.

Since the transformations O describe rotations of the marker device 2, and therefore the associated co-ordinate system $C_m$, about the point p, the equation $O*p'=p'$ must be fulfilled. The reason is that the location of the point p in the co-ordinate system $C_m$ is invariant if the marker device 2, and thus the co-ordinate system $C_m$, is rotated about the point p. With the N transformations $O_1$ to $O_N$, this results in a system of N equations $O_1*p'=p'$ to $O_N*p'=p'$. This system of equations can be solved by known mathematical approaches in order to determine the location of the point p, which is the center of rotation of the femur.

It shall be noted that step S07 is optional. Instead of compensating the displacement of the camera, image pairs for which the displacement of the camera is above a predetermined threshold can be discarded. As an alternative, calculating the center of rotation in step S10 involves weighting the transformations associated with the image pairs depending on the displacement of the camera 3 associated with the respective image pairs.

As an option, the method can continue with a step S11 subsequent to step S10, wherein S11 involves determining whether or not the accuracy of the location of the center of rotation p of the femur 1 is above a predetermined threshold. If this is not the case, additional image pairs are formed in analogy to step S02 and steps S03 to S09 are performed for the additional image pairs. Step S10 is then repeated for the transformations associated with both the initial image pairs and the additional image pairs.

There are several approaches for determining the displacement of the camera 3 in step S06.

One approach is to attach a marker device to the camera 3 and to track the marker device, and therefore the camera 3, using a stationary camera.

Another approach involves analyzing and integrating data output by inertial sensors attached to the camera 3 between t1 and t2, thus obtaining the displacement of the camera 3.

Still another approach involves identifying identical points in space in both images of an image pair and calculating the displacement of the camera 3 from the differences of the positions at which those points in space are imaged in the two images of the image pair. The points in space are for example points on a stationary object, such as the object 4 shown in FIG. 2. The points in space for example are easily recognizable points, such as points on edges or corners of the stationary object 4.

It shall be noted that, from a mathematical point of view, it is sufficient to determine the displacement of the camera 3 in five degrees of freedom, because it is known that the transformation O is a rotation about the point p.

In this case, for example, the rotation of the camera 3 can be determined, but the translational movement of the camera 3 can not be fully determined. In one embodiment, only the line in space on which the camera 3 is displaced can be determined, but not the distance, which also includes the direction of the movement along the line in space. This means that $T_c$ is known except for a scale factor of the translation. This might occur if the displacement of the camera 3 is determined from identical points in space and their locations within the images of the image pairs.

If $O*p'=p'$, then also $O^{-1}*p'=p'$. With $O=P_1*T_C^{-1}*P_2^{-1}$, this leads to $$(P_2*T_c*P_1^{-1})*p'=p'.$$

If $P_1$, $P_2$ and $T_c$ are divided into rotational components $P_{1R}$, $P_{2R}$ and $T_{cR}$ and translational components $P_{1T}$, $P_{2T}$ and $T_{cT}$, respectively, in analogy to O being divided into R and T and $T_{cT}$ is associated with an unknown scale factor a, then $$P_{2R}*(T_{cR}(P_{1R}^{-1}*p+P_{1T}^{-1})+(a*T_{cT}))+P_{2T}=p.$$

This can be rewritten into $$\begin{pmatrix} S_1 & A_1 & 0 & 0 & \ldots & 0 \\ S_2 & 0 & A_2 & 0 & \ldots & 0 \\ S_3 & 0 & 0 & A_3 & \ldots & 0 \\ \vdots & \vdots & \vdots & \vdots & & \vdots \\ S_N & 0 & 0 & 0 & \ldots & A_N \end{pmatrix} * \begin{pmatrix} x \\ y \\ z \\ a_1 \\ a_2 \\ a_3 \\ \vdots \\ a_N \end{pmatrix} = \begin{pmatrix} B_1 \\ B_2 \\ B_3 \\ \vdots \\ B_N \end{pmatrix}$$

with $S_n = P_{2R\_n} * T_{cR\_n} * P_{1R\_n}^{-1} - 1)$ $A_n = P_{2R\_n} * T_{cT\_n}$ and $B_n = -(P_{2R\_n} * T_{cR\_n} * P_{1T\_n}^{-1} + P_{2Ti})$, wherein I is the unity matrix and n is an index of the N measured transformations. The co-ordinates x, y and z of the point p and the scale factor a can be determined by solving the above system of equations.

Figure 5:
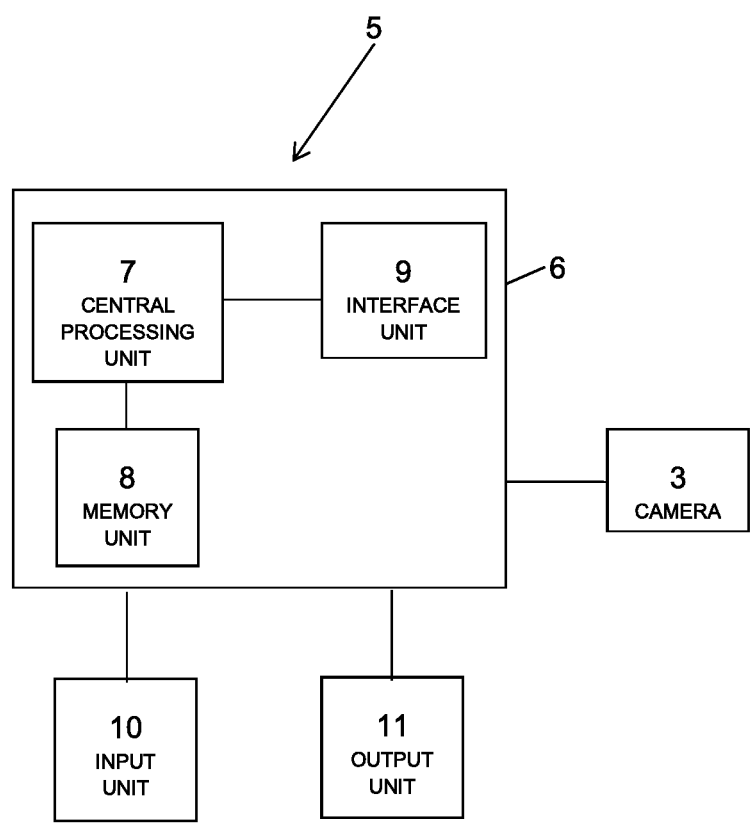

FIG. 5 schematically shows a system 5 which implements the present invention. It comprises a computer 6 being connected to the camera 3. The computer 6 comprises a central processing unit 7, a memory unit 8 and an interface unit 9. Via the interface unit 9, the computer 6 is connected to the camera 3. However, the interface unit 9 can also be used to acquire the image data, for example from a storage unit, if the computer 6 is not connected to the camera 3. The memory unit 8 stores working data, such as the image data, the relative positions and the transformations associated with the image pairs and the location of the center of rotation, and a computer program which instructs the central processing unit 7 to perform the method described herein.

Connected to the computer 6 is an input unit 10 for receiving user input, such as a keyboard, a mouse, a touch sensitive surface or the like. The computer 6 is further connected to an output unit 11, such as a display unit, which can for example display the camera images, such as an image as shown in FIG. 2.

As an option, the method comprises an additional step of calculating at least one overlay image, which is a camera image, for example from the plurality of images, in which the location of the center of rotation p is overlaid. Since the relative position of the marker device 2 and the camera 3 is known, because it was calculated in step S04 or step S05, and the location of the center of rotation p relative to the marker device was calculated in step S10, the location of the point p can be projected into the camera image. If the at least one overlay image is displayed on a display unit, the location of the center of rotation can be verified by a user of the system 5, for example by inputting verification information via the input unit 10.

The invention claimed is:

1. A computer implemented method for determining a center of rotation of a bone, comprising the steps of:
    acquiring image data representing a plurality of images taken by a camera while the bone is being rotated about the center of rotation, wherein the images show a marker device attached to the bone;
    forming a plurality of image pairs from the image data, wherein each image pair comprises two different images;
    for each of the plurality of image pairs, obtaining transformations by:
        determining a first relative position of the marker device relative to the camera from a first image of an image pair;
        determining a second relative position of the marker device relative to the camera from a second image of the same image pair; and,
        calculating a transformation of the first relative position into the second relative position;
    calculating the location of the center of rotation of the bone relative to the marker device from the plurality of obtained transformations for each of the plurality of image pairs.

2. The method of claim 1, further comprising the step of determining, for each image pair, a displacement of the camera between the points in time at which the images of the respective image pair were captured.

3. The method of claim 2, wherein calculating the location of the center of rotation of the bone includes weighting the transformations depending on the displacements of the camera associated with the corresponding image pairs.

4. The method of claim 2, further comprising the step of amending the first relative position or the second relative position associated with an image pair to compensate the displacement of the camera if the displacement associated with the corresponding image pair is above a predetermined threshold.

5. The method of claim 4, wherein amending a relative position involves one of subtracting the displacement of the camera from the relative position or adding the displacement of the camera to the relative position.

6. The method of claim 2, wherein the displacement of the camera is calculated from sensor data acquired from an inertial sensor attached to the camera.

7. The method of claim 2, wherein the displacement of the camera is calculated from differences of positions within the first and second images of an image pair which show the same points in space.

8. The method of claim 7, wherein a point in space is not a point on a marker device.

9. The method of claim 1, wherein a pair of images comprises two consecutive images.

10. The method of claim 1, wherein the transformation is represented by a 4×4 matrix.

11. The method of claim 1, further comprising:
    forming additional image pairs,
    obtaining an additional transformation for each of the additional image pairs;
    adding the additional transformation corresponding to each of the additional image pairs to the plurality of transformations for the plurality of image pairs to create a new plurality of transformations; and,
    calculating the location of the center of rotation of the bone relative to the marker device for the new plurality of transformations if an accuracy of the location of the center of rotation is below a predetermined threshold.

12. The method of claim 1, wherein the relative position of the marker device relative to the camera is the position of a co-ordinate system associated with the marker device in a co-ordinate system associated with the camera.

13. The method of claim 1, wherein calculating a transformation of a first relative position into a second relative position takes into account that the transformation is a rotation about a fixed point or axis in space.

14. A non-transitory computer-readable program storage medium storing a computer program which, when executed by at least one processor of at least one computer, causes the computer to determine a center of rotation of a bone, comprising the steps of:
- acquiring image data representing a plurality of images taken by a camera while the bone is being rotated about the center of rotation, wherein the images show a marker device attached to the bone;
- forming a plurality of image pairs from the image data, wherein each image pair comprises two different images;
- for each of the plurality of image pairs, obtaining transformations by:
  - determining a first relative position of the marker device relative to the camera from a first image of an image pair;
  - determining a second relative position of the marker device relative to the camera from a second image of the same image pair; and,
  - calculating a transformation of the first relative position into the second relative position;
- calculating the location of the center of rotation of the bone relative to the marker device from the plurality of obtained transformations for each of the plurality of image pairs.

15. A system comprising at least one computer having at least one processor configured to determine a center of rotation of a bone, comprising:
- acquire image data representing a plurality of images taken by a camera while the bone is being rotated about the center of rotation, wherein the images show a marker device attached to the bone;
- form a plurality of image pairs from the image data, wherein each image pair comprises two different images;
- for each of the plurality of image pairs, obtaining transformations by:
  - determining a first relative position of the marker device relative to the camera from a first image of an image pair;
  - determining a second relative position of the marker device relative to the camera from a second image of the same image pair; and,
  - calculating a transformation of the first relative position into the second relative position;
- calculating the location of the center of rotation of the bone relative to the marker device from the plurality of obtained transformations for each of the plurality of image pairs.

* * * * *